United States Patent
Koch

(10) Patent No.: US 6,202,898 B1
(45) Date of Patent: Mar. 20, 2001

(54) DEVICE FOR SUPPLYING MEDICAL INSTRUMENTS WITH A FLUID IN PARTICULAR WITH A RINSING FLUID

(75) Inventor: Guido Koch, Karlsruhe (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 09/292,413

(22) Filed: Apr. 15, 1999

(30) Foreign Application Priority Data

Apr. 17, 1998 (DE) ............................................. 198 17 173

(51) Int. Cl.[7] .................................................. B65D 83/00
(52) U.S. Cl. ......................................................... 222/400.7
(58) Field of Search ............................ 222/82, 394, 399, 222/400.7, 325; 604/141, 142, 217, 405

(56) References Cited

U.S. PATENT DOCUMENTS 4,997,111 * 3/1991 Lowers .................................. 222/399
5,114,033 * 5/1992 Golias et al. ........................... 222/82
5,836,483 * 11/1998 Disel ..................................... 222/396

FOREIGN PATENT DOCUMENTS 297 00 763
U1    6/1998  (DE) .

* cited by examiner

Primary Examiner—Kevin Shaver
Assistant Examiner—David Deal
(74) Attorney, Agent, or Firm—Akin, Gump, Strauss, Hauer & Feld, L.L.P.

(57) ABSTRACT

With this device the fluid is located in a container which can be set under pressure, into which two cannulas of differing lengths may be inserted. A short cannula, via a gas conduit and a release valve, is connectable to a pressurised gas source in order to impinge the container above the fluid level with pressurised gas, whilst the other longer cannula is connectable to a fluid conduit leading to the instrument and protrudes into the fluid located in the container. The fluid flow to the instrument is interruptable with a blocking element and the pressurised gas supply to the container is interruptable with the release valve. Such a device may be simply constructed and used when, according to the invention, the cannulas, the blocking element and a control valve are grouped together into a constructional unit on which there is located one connection for the gas conduit and a further connection for the fluid conduit.

14 Claims, 2 Drawing Sheets

DEVICE FOR SUPPLYING MEDICAL INSTRUMENTS WITH A FLUID IN PARTICULAR WITH A RINSING FLUID

BACKGROUND OF THE INVENTION

The invention relates to a device for supplying medical instruments with a fluid, in particular a rinsing fluid, which is located in a container which can be set under pressure and into which two cannulas of a differing length may be inserted, wherein a short cannula, via a gas conduit and a release valve, is connectable to a pressurised gas source in order to impinge the container above the fluid level with pressurised gas, whilst the other longer cannula is connectable to a fluid conduit leading to the instrument and protrudes into the fluid located in the container and wherein the fluid flow to the instrument is interruptable with a blocking element and the pressurised gas supply to the container is interruptable with the release valve.

The delivery of fluid such as for example sterilised salt solution to the instrument, is introduced in the manner that a release valve is actuated via a foot switch and then pressurised gas from the pressurised gas source via the release valve impinges the fluid level of the fluid located in the container. The fluid conduit may be blocked or released via a blocking element. If the blocking element is in the release position the fluid on account of the gas pressure acting on it flows across the blocking element to the instrument, which for example comprise optics whose distal lens or distal window, with the fluid exiting from a nozzle, is rinsed free of impurities such as secretion, smoke particles and likewise, at certain time intervals, in order to offer the operator a good viewing through the optics. In order to interrupt the rinsing procedure it is not sufficient to interrupt the pressure supply from the pressurised air source, since the pressure in the container on account of the stored gas volume only sinks slowly and thus the rinsing would continue for a while.

The blocking element is mostly a tubing squeezer into which as a fluid conduit there is applied a flexible tubing, which e.g. is squeezed or released via an electromagnetically actuated pluger, wherein this together with the release valve may be controlled in its function by way of the foot switch.

A disadvantage of these known devices is that several device parts are to be handled and operated differently and separately, such as the connection of the pressurised gas conduit to the pressure source across the release valve to the shorter cannula, furthermore the connection of the fluid conduit to the longer cannula, the insertion of the fluid conduit into the blocking element and the connection to the medical instrument. Furthermore firstly the shorter cannula is to be inserted through a container closure and to be positioned above the fluid level. Subsequently or previously the longer cannula is to be handled similarly but this must be incorporated into the container such that it submerses adequately deeply into the fluid. With all these quite complicated activities also confusions of parts when making the respective connections are not to be ruled out so that there exists a considerable potential risk of error.

BRIEF SUMMARY OF THE INVENTION

It is the object of the invention to considerably simplify the application of such a device in order by way of this to rule out possible sources of errors with respect to the handling and functioning with a high security. Furthermore the device is to be manufacturable simply and cheaply.

The solution of the object lies in the fact that the cannulas, the blocking element and a control valve are grouped together into a constructional unit on which there is located one connection for the gas conduit and a further connection for the fluid conduit. By way of this a one-piece construction of the device is given, with which it is no longer necessary to have to manipulate the cannulas individually, and with whose connections the conduits may be simply connected. The blocking of the gas supply is effected in this case directly in the constructional unit by the control valve, wherein the gas supply conduit is bled.

Furthermore it is provided that the connections of the tubings are formed differently so that a connection confusion of the gas and fluid conduits formed correspondingly differently may no longer occur. The two cannulas are grouped together such that the longer cannula is surrounded at a distance by the shorter cannula coaxially and whilst forming a pressurised gas channel.

The shorter cannula at its end directed to the fluid level is provided with openings through which the pressurised gas may flow into the inside of the container in order to impinge the fluid level with pressure. The length of the shorter cannula is matched such that this ends above the fluid level, whilst the length of the other cannula is submersed into the fluid to a predetermined degree. Both cannulas are rigidly connected to one another as parts of the constructional unit so that compellingly they may only be inserted commonly into the container and with this assume the correct position with respect to insertion depth.

Furthermore the control valve and the blocking element are grouped together as a common valve and integrated into the constructional unit. This valve consists of a valve housing which axially movably accommodates a valve slider which seals on the circumference. The valve slider can be moved out of an initial position into an operating position, wherein the initial position is assumed by the force of a spring. The operating position is achieved by the pressure force which results from the gas pressure and the pressure-effective end face of the valve slider, which is distant to the spring side.

The valve slider comprises valve control edges for the pressurised gas as well as valve control edges for the fluid which in each case correspond to control openings incorporated into the housing in the operating position.

In the initial position by way of the position of the valve slider the pressurised gas conduit just as the fluid conduit are blocked from the container space towards the medical instrument.

In the operating position the valve slider releases the further conduit of the pressurised gas from the gas conduit, via the channel formed between the cannulas, by which means the gas pressure acts on the fluid level. At the same time the valve slider however also releases the transport of the fluid via the longer cannula into the fluid conduit towards the medical instrument. If the release valve e.g. operable by foot, is formed between the pressurised gas source and the constructional unit according to the invention, as a 3/2 valve, the gas conduit between the release valve and the constructional unit is bled whilst the container continues to be under pressure.

In another formation the valve slider may be so formed on its side distant to the spring that this side for example accommodates an elastomer seal which cooperates with a valve seat which is part of the pressurised gas valve. In the initial position the elastomer seal by way of the force of the spring is sealingly pressed against the valve seat and thus the pressurized gas supply towards the container is blocked.

Furthermore it is possible to realise the backflow of the gas out of the container by way of an integrated check valve instead of by way of the valve slider. The check valve with this is located between the gas conduit and the cannula in the valve housing so that preceding from the pressurised gas source with an open check valve a free flow for the pressurised gas is given. The opposite flow direction is blocked by the check function. With such a connecting arrangement then the check valve ensures that the container space above the fluid level is not then bled. Because the valve slider after bleeding the gas conduit is brought into the initial position by the force of the spring, also the fluid flow through the valve slider is immediately blocked. With the initiation of a further rinsing procedure thus the container space above the fluid level need not be filled again with pressurised gas. This permits a rapid start of the rinsing procedure after activation of the release valve.

The control of the fluid supply in the outlined manner brings savings in the manufacture and in the subsequent maintenance and also increases the reliability in the practical application.

BRIEF DESCRIPTION OF THE DRAWINGS

The invention is hereinafter described in more detail by way of embodiment examples and the accompanying drawing. There are shown.

DETAILED DESCRIPTION OF THE INVENTION

Figure 1:
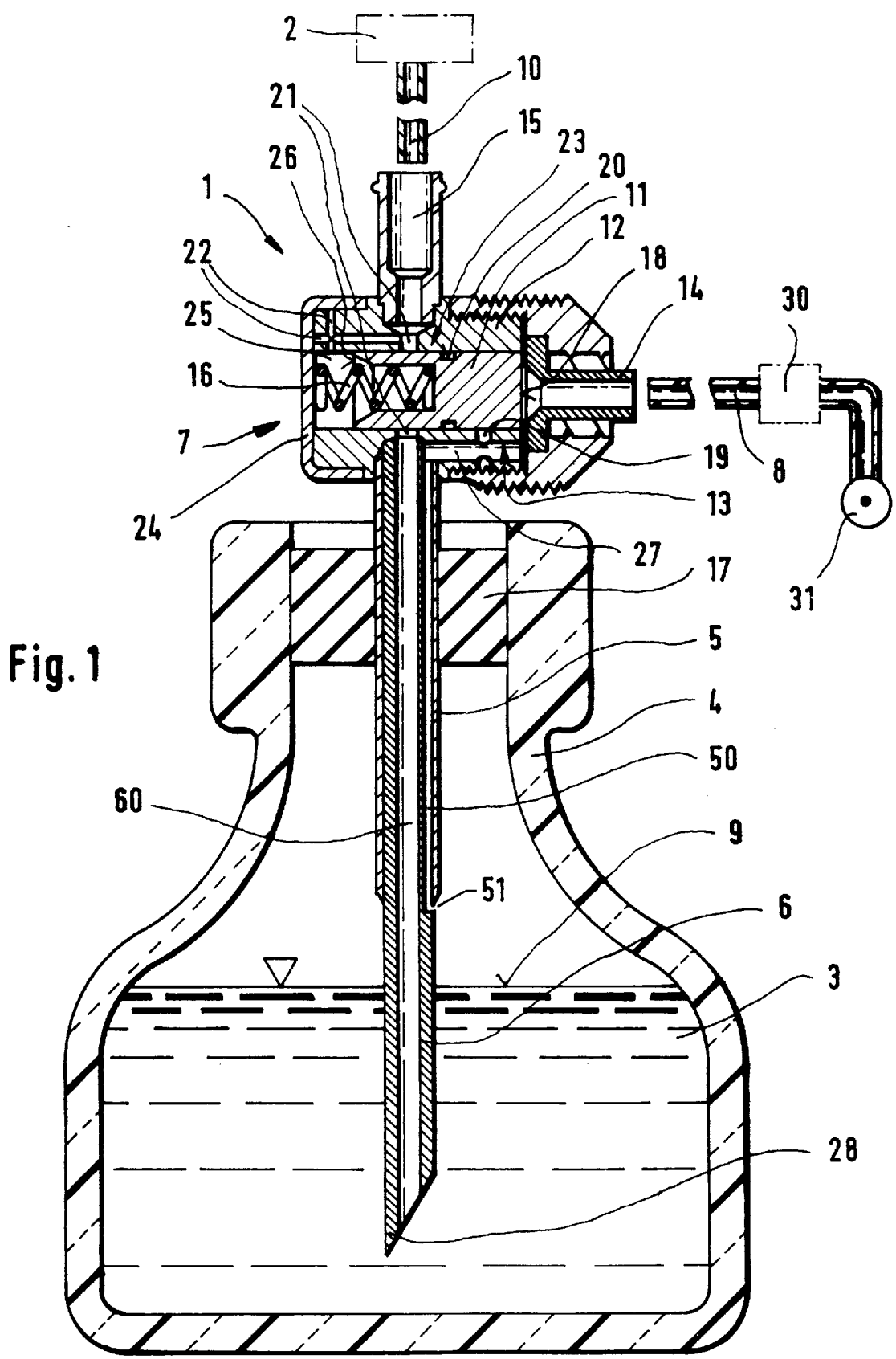
FIG. 1 a device according to the invention in a sectional representation, together with a container filled partly with fluid, and FIG. 2 a further embodiment example in a sectional representation.

In FIG. 1 the constructional unit 1 of the device for supplying medical instruments 2 with fluid, in a pressure tight manner is pierced through a container closure 17 with the two cannulas 5,6 arranged coaxially to one another. Both cannulas are of a different length. In order to simplify the procedure of piercing, the longer cannula 6 is provided with a point 28 at its free end.

The longer cannula 6 submerses into the fluid 3 up to a predetermined depth, whilst the shorter cannula 5 opens with at least one opening 51 into the container above the fluid level 9.

The two cannulas 5, 6 are rigid parts of the constructional unit 1. This constructional unit also comprises a control valve for the pressurised gas control and a blocking element for the fluid control in one unit as a valve 7. This valve 7 consists of a valve housing 12 into which a valve slider 11 as a blocking element is axially movable but also at the same time is radially mounted against the valve housing 12 in a sealing manner.

The valve housing 12 and the valve slider 11 thus in a part region 13 of the valve 7 assume the control of the pressurised gas which is supplied from a pressurised gas source 31 via a release valve 30, a gas conduit 8 and a pressurised gas connection piece 14 to the part region 13 of the valve 7 for the control of pressurised gas.

In a further part region 23 the valve housing 12 and the valve slider 11 assume the control of the flow of the fluid 3 which according to the position of the valve slider may be released or blocked.

In the following function example the valve 7 is firstly in an initial position. The gas pressure prevailing from the pressurised gas source 31 blocks the release valve 30 and does not prevail at the valve 7. In this initial condition the force of a spring 16 acts against the valve slider 11 and has the effect that the valve slider with its control edge 18 is brought to bear on the connection piece 14 on the pressurised gas side. The pressurised gas control opening 19 in the valve housing 12 is blocked by the valve slider 11 in the part region 13 of the valve 7. In the part region 23 which is allocated to the control of the fluid the valve control edges 20 of the valve slider 11 are likewise not located overlapping with the fluid control openings 21. Thus in this switching position the fluid flow from the container 4 through the cannula 6 towards the medical instrument 2 through the valve 7 is likewise blocked.

The radially sealing, axially movable mounting of the valve slider 11 in the valve housing 12 as a rule ensures that the pressurised gas part region 13 is likewise sealed against the fluid part region 23.

If the release valve 30 is actuated, pressurised gas flows through the conduit 8 onto the end face of the valve slider 11, which is distant to the spring 16. On account of the force exerted onto this end face by the pressurised gas, the valve slider 11 displaces against the force of the spring 16 and comes to bear on the valve lid 24 on the spring side. In this operating position on the pressurised gas side from now on there arises a connection from the pressurised gas source 31 via the release valve 30 and the gas conduit 8 into the valve 7. The pressurised gas control edge 18 has released the pressurised gas control opening 19, and the pressurised gas flows via a connecting channel 27 and a pressurised gas flow channel 50 between the coaxial cannulas out of the pressurised gas exit 51 and exerts a pressure force onto the fluid level 9. Since in this operating position the fluid control edges 20 likewise are located overlapping with the fluid control openings, the pressure force above the fluid level 9 has the effect that fluid 3 is supplied through the inner space 60 of the longer cannula 6, through the valve 7, fluid connection piece 15, and the fluid conduit 10 to the medical instrument 2. On switching off the pressurised gas supply through the release valve the gas conduit 8 is bled. The force of the spring 16 on the valve slider 11 may again be effective and move back the valve slider into the previously described initial position so that the supply of fluid 3 towards the instrument 2 as well as the backflow of the pressurised gas from the container in the direction of the gas conduit 8 is interrupted.

Figure 2:
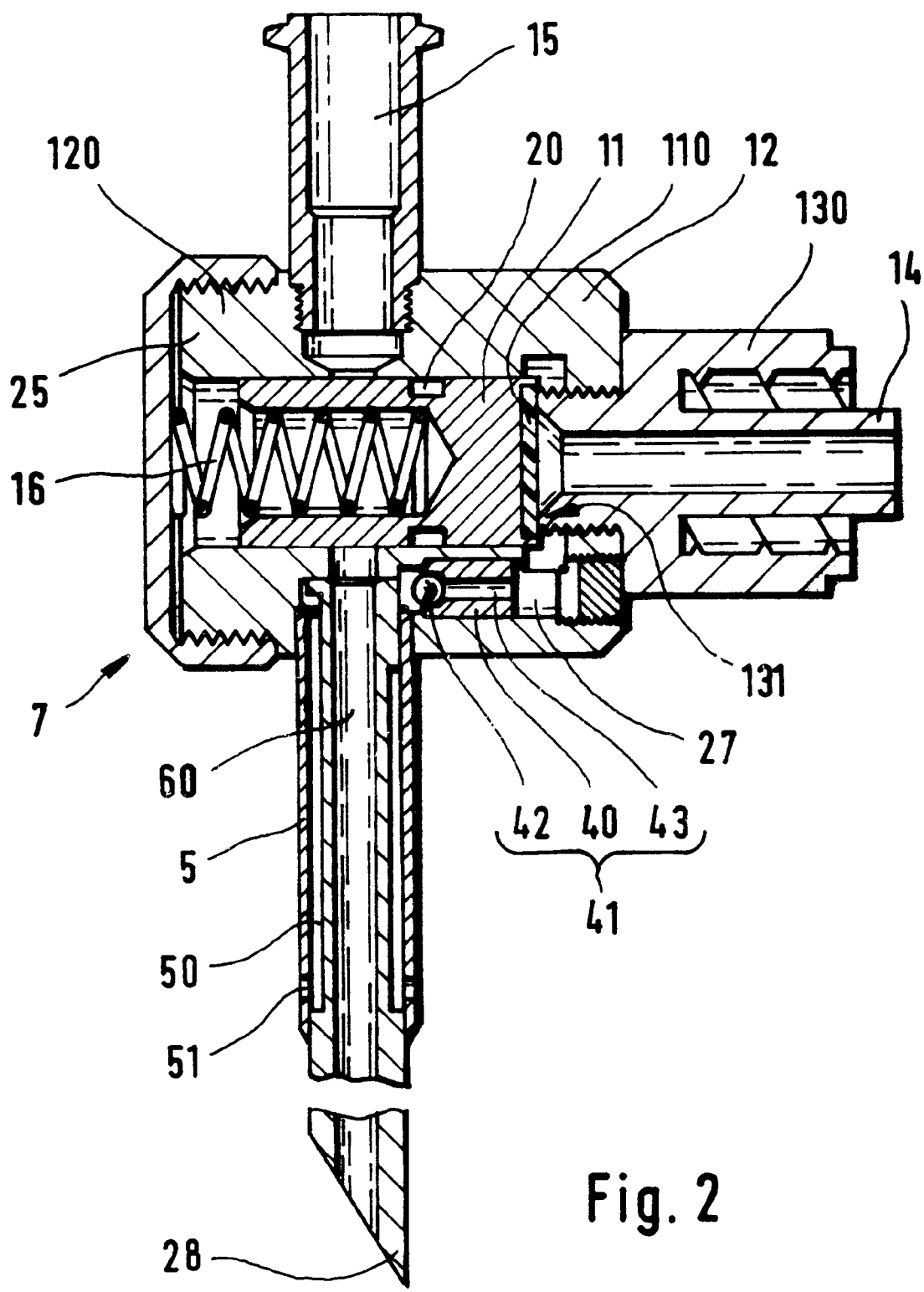

The backflow of the pressurised gas may, as FIG. 2 shows, alternatively also be interrupted by a check valve 41. In a simple embodiment this may consist of a valve insert 40 incorporated into the connection channel, with an axial gas passage 43 and a sealing element 42. The check valve 41 is to be incorporated into the valve housing 12 such that a free flow-through from the pressurised gas source 31 into the container 4 is given. In the opposite direction of flow the sealing element 42 here formed as a ball blocks the valve 7 and prevents a gas backflow.

Furthermore it is possible for increasing the sealing effect to provide a seal 110 which the valve slider 11 in the idle position is presses against the valve seat 131 of the pressurized gas connection piece 130 by the spring force. Should in this position of the valve 7 a fluid leakage result via the valve slider 11 into the space 25 of the valve housing 12, e.g. by way of a principly caused leak of a seallessly fitted-in valve slider 11 into the valve housing, this fluid leakage is led off in the region 120 of the valve housing 12 via leakage bores 22 which according to FIG. 1 are specially incorporated into the valve housing 12, into the pressureless fluid conduit 10. Thus fluid collected in the space 25 may escape with actuation of the valve slider 11.

The achievable advantages of this invention lie particularly in the fact that a multitude of components which otherwise with the known devices are to be handled individually, from now on are grouped together and integrated in a constructional unit and the control is reduced to one element, the pressurised gas conduit. Unmistakable on the constructional unit are also the connections of the pressurised gas conduit and the fluid conduit, since these are formed differently. By way of this there is made available a compact, simply constructed and above all reliable device for supplying in particular medical instruments, but also medical apparatus and likewise, with a fluid. By way of the suggested construction according to the invention above all the handling and functioning risk is reduced to a measure which cannot be limited any further.

What is claimed is:

1. A device for supplying medical instruments with a fluid located in a container which is set under pressure by a pressurized gas supplied to the container via a gas conduit and a release valve and thereby forced through a fluid conduit leading to the instrument, the device comprising a control valve unit having (a) a first connection for connection with the gas conduit,
   (b) a second connection for connection to the fluid conduit,
   (c) a short cannula having a first end interruptably connected to the first connection and a second end for insertion into the container above a level of the fluid located in the container and for impinging the fluid located in the container with the pressurized gas,
   (d) a long cannula having a length greater than a length of the short cannula and having a first end interruptably connected to the second connection and a second end for protruding into the fluid located in the container, and
   (e) a blocking element for interrupting the connection of the long cannula to the second connection and for interrupting the connection of the short cannula to the first connection upon switching off the release valve.

2. The device according to claim 1, wherein the first and second connections are formed as connection pieces for tubings and have different forms.

3. The device according to claim 1, wherein the long cannula is surrounded by the short cannula in a coaxial and radially spaced manner to form a pressurized gas flow channel, and wherein both cannulas are rigidly connected to one another.

4. The device according to claim 1, wherein the control valve unit comprises a slider valve, and the blocking element comprises a longitudinally movable valve slider integrated into the valve unit.

5. The device according to claim 4, wherein the valve slider is displaceable from an initial position into an operating position and is biased by a spring in a direction of its initial position.

6. The device according to claim 5, wherein an end face of the valve slider, which is distant from the spring, comprises a valve control edge for release and blocking of the pressurized gas flow into and out of the container.

7. The device according to claim 5, wherein an end face of the valve slider, which is distant from the spring, is provided with a seal.

8. The device according to claim 7, wherein the seal cooperates with the valve slider.

9. The device according to claim 1, wherein backflow of the pressurized gas from the container to the release valve is blocked via a check valve.

10. The device according to claim 1, wherein the blocking element is biased to a connection interrupting position by a spring in the control valve unit.

11. The device according to claim 1, wherein the blocking element is biased to an open, non-interrupting position by admission of the pressurized gas through the first connector.

12. The device according to claim 11, wherein the blocking element has fluid control edges which in the open, non-interrupting position are in alignment with the second connection and the long cannula, so as to allow fluid flow therethrough.

13. The device according to claim 11, wherein the control valve has an opening which lies beyond an end of the blocking element in the open, non-interrupting position, so as to allow pressurized gas flow therethrough, but the opening is blocked by the blocking element in a connection interrupting position.

14. The device according to claim 1, wherein the fluid is a rinsing fluid.

* * * * *